United States Patent [19]

Agarwal

[11] Patent Number: 5,817,053
[45] Date of Patent: Oct. 6, 1998

[54] GUIDE CATHETER EXCHANGE DEVICE

[75] Inventor: Jai B. Agarwal, Somerset, N.J.

[73] Assignee: University of Medicine & Dentistry of NJ, Newark, N.J.

[21] Appl. No.: 569,277

[22] Filed: Dec. 8, 1995

[51] Int. Cl.$^6$ .................................................. A61M 31/00
[52] U.S. Cl. ........................... 604/53; 604/264; 604/164; 128/772
[58] Field of Search ..................................... 604/108, 264, 604/280, 164, 158, 282; 128/642, 772; 606/41, 100, 194

[56] References Cited

U.S. PATENT DOCUMENTS 5,571,094 11/1996 Sirhan ..................................... 604/284

Primary Examiner—Mark Bockelman
Assistant Examiner—N. Kent Gring
Attorney, Agent, or Firm—Richard R. Muccino

[57] ABSTRACT

The present invention pertains to guide catheter exchange devices for exchanging a guide catheter advanced over a balloon catheter and a coronary guide wire without removing the coronary guide wire in percutaneous transluminal coronary angioplasty. In one embodiment, the invention pertains to a guide catheter exchange device for exchanging a guide catheter employed by a over-the-wire balloon catheter. In this embodiment, the exchange device comprises Section 1, Section 2, and a connecting device for connecting Section 1 and Section 2. Section 1 is a hollow wire having a soft tip, an inner diameter from about 0.012 inches to about 0.020 inches, an outer diameter from about 0.030 inches to about 0.040 inches, and a length from about 120 centimeters to about 160 centimeters. Section 2 is a hollow coiled wire having an inner diameter from about 0.012 inches to about 0.020 inches, an outer diameter from about 0.030 inches to about 0.040 inches, and a length from about 120 centimeters to about 160 centimeters. In another embodiment, the invention pertains to a guide catheter exchange device for exchanging a guide catheter employed by a monorail balloon catheter. In this embodiment, the exchange device comprises a wire having a length from about 200 centimeters to about 240 centimeters and an outer diameter from about 0.030 inches to about 0.040 inches. The distal end of the exchange device is hollow, has a length from about 40 centimeters to about 60 centimeters, an inner diameter from about 0.012 inches to about 0.020 inches, and a side hole from about 40 centimeters to about 60 centimeters from the distal end of the exchange device through which the coronary guide wire may pass. The proximal end of the exchange device is hollow or solid, has an outer diameter from about 0.030 inches to about 0.040 inches, and a length from about 150 centimeters to about 200 centimeters. The present invention also pertains to methods for using the guide catheter exchange devices of the present invention.

11 Claims, 4 Drawing Sheets

GUIDE CATHETER EXCHANGE DEVICE

BACKGROUND OF THE INVENTION

1. Field of the Invention

The present invention pertains to guide catheter exchange devices for exchanging a guide catheter advanced over a balloon catheter and a coronary guide wire without removing the coronary guide wire in percutaneous transluminal coronary angioplasty. In one embodiment, the invention pertains to a guide catheter exchange device for exchanging a guide catheter employed by a over-the-wire balloon catheter. In this embodiment, the exchange device comprises Section 1, Section 2, and a connecting device for connecting Section 1 and Section 2. Section 1 is a hollow wire having a soft tip, an inner diameter from about 0.012 inches to about 0.020 inches, an outer diameter from about 0.030 inches to about 0.040 inches, and a length from about 120 centimeters to about 160 centimeters. Section 2 is a hollow coiled wire having an inner diameter from about 0.012 inches to about 0.020 inches, an outer diameter from about 0.030 inches to about 0.040 inches, and a length from about 120 centimeters to about 160 centimeters. In another embodiment, the invention pertains to a guide catheter exchange device for exchanging a guide catheter employed by a monorail balloon catheter. In this embodiment, the exchange device comprises a wire having a length from about 200 centimeters to about 240 centimeters and an outer diameter from about 0.030 inches to about 0.040 inches. The distal end of the exchange device is hollow, has a length from about 40 centimeters to about 60 centimeters, an inner diameter from about 0.012 inches to about 0.020 inches, and a side hole from about 40 centimeters to about 60 centimeters from the distal end of the exchange device through which the coronary guide wire may pass. The proximal end of the exchange device is hollow or solid, has an outer diameter from about 0.030 inches to about 0.040 inches, and a length from about 150 centimeters to about 200 centimeters. The present invention also pertains to methods for using the guide catheter exchange devices of the present invention.

2. Description of the Background

Coronary angioplasty is the surgical reconstitution or recanalization of a narrowed or blocked coronary artery. Percutaneous transluminal coronary angioplasty (PTCA) is a technique performed through the skin (percutaneous) inside an artery (transluminal) of the heart (coronary) to reshape (angioplasty) that artery. In percutaneous transluminal coronary angioplasty, a puncture is made in an artery of the leg with a hollow needle. A guiding wire, about 0.035 inch in outer diameter and 145 centimeters long, is then passed through this hollow needle. After this guiding wire is passed into the aorta, a hollow tube, called a sheath, is inserted over the guiding wire into the artery. When the sheath is in place, a specially shaped hollow tube, called a guide catheter (FIG. 1, A) having an internal diameter from about 2 mm to about 3 mm and about 100 centimeter long, is inserted through the sheath, over the guiding wire, and advanced to the aorta. The guide catheter is positioned at the ostium of the coronary artery and does not enter it. Once this guide catheter is positioned at the ostium of the coronary artery, a balloon catheter (FIG. 1, B) is inserted through the guide catheter. Inside the balloon catheter is a very fine wire called a coronary guide wire (FIG. 1, C) which can vary in size from about 0.010 inch to about 0.018 inch in outer diameter and is usually from about 300 centimeters to about 175 centimeters long. The coronary guide wire is used to reach inside the coronary artery and can be steered to enter into various branches. The coronary guide wire has a flexible tip, only a few centimeters long, which can be bent into different shapes. Once this coronary guide wire has crossed the blockage in the coronary artery, and has been placed properly in the distal part of the artery, the balloon catheter is advanced over the coronary guide wire into the coronary artery. When the balloon catheter crosses the blockage, it can be inflated by a device to a pressure from about 1 to about 25 atmospheres. Balloon catheters are typically about 0.030 inches in outer diameter when not inflated and about 1.5 mm to 4 mm when inflated. When the balloon catheter is inflated inside the artery, the balloon stretches the intima leaving a ragged interior surface after deflation. This stretching of the intima breaks up the plaque producing an enlarged lumen.

Usually it is easy to advance the balloon catheter over the coronary guide wire and across the blockage. Sometimes, however, the guide catheter backs out from the ostium of the coronary artery when the balloon catheter is advanced and the balloon catheter cannot cross the blockage. In such cases, it may be necessary to exchange the guide catheter for another guide catheter with a different shape. However, once the coronary guide wire has already crossed the blockage, it is undesirable to pull the coronary guide wire back from the blockage to exchange the guide catheter since this exchange can lengthen the procedure and increase patient risk. Exchanging the guide catheter over the coronary guide wire is also undesirable because coronary guide wires are very thin, only about 0.010 to about 0.018 inches in diameter, and do not provide adequate support for exchanging the guide catheter making the procedure unpredictable. At present, there are no satisfactory systems available to exchange the guide catheter once the coronary guide wire has crossed the blockage in the coronary arteries.

A report in *Catherization and Cardiovascular Diagnosis* 33, pp. 284–287 (1994) describes a guide catheter exchange device that is 282 cm in length and is compatible with guide wires up to about 0.018 inches in diameter. The catheter is reported to contain two inner lumens and four ports providing a partial monorail design and the exchange technique requires a moderate amount of operator skill and a learning curve. The exchange of the guide catheter requires threading the coronary guide wire through an exit port of the exchange device located 120 cm proximal to the distal tip of the device and reinserting the coronary guide wire through a re-entry port of the exchange device located 130 cm proximal to the distal tip of the device.

SUMMARY OF THE INVENTION

Figure 1:
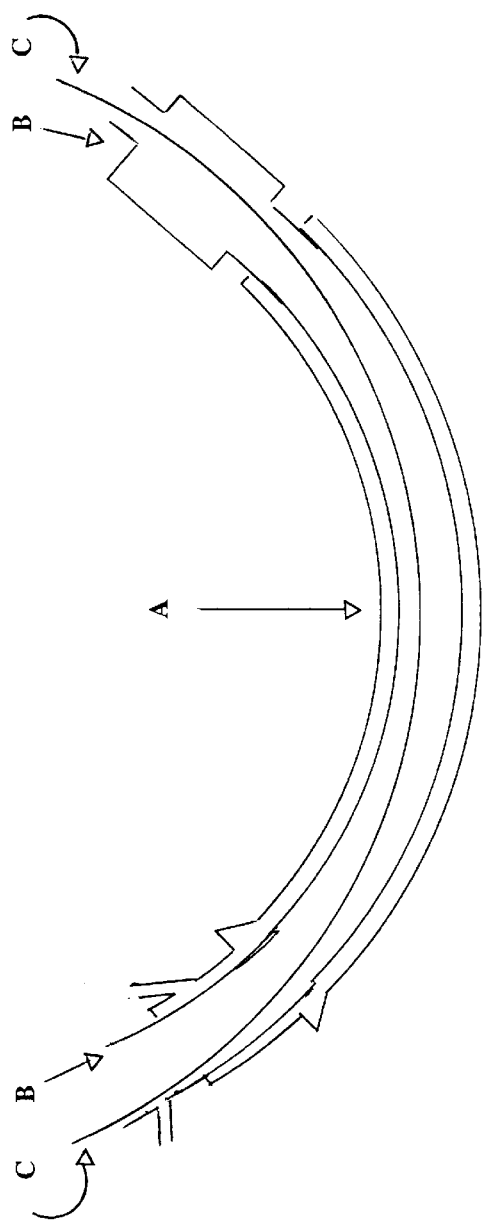
FIG. 1 illustrates a conventional guide catheter advanced over an over-the-wire balloon catheter and a coronary guide wire.

The present invention pertains to a method for exchanging a guide catheter employed by an over-the-wire balloon catheter in percutaneous transluminal coronary angioplasty which comprises the steps of:

(a) providing a first guide catheter advanced over an over-the-wire balloon catheter and a coronary guide wire, wherein the first guide catheter is in the ostium of a coronary artery and proximal to a blockage;

(b) providing a guide catheter exchange device comprising Section 1, Section 2, and a connecting device for connecting Section 1 and Section 2; wherein Section 1 is a hollow wire having an inner diameter from about 0.012 inches to about 0.020 inches, an outer diameter from about 0.030 inches to about 0.040 inches, and a length from about 120 centimeters to about 160 centimeters; and Section 2 is a hollow wire having an inner diameter from about 0.012 inches to about 0.020 inches, an outer diameter from about 0.030 inches to about 0.040 inches, and a length from about 120 centimeters to about 160 centimeters;

(c) removing the over-the-wire balloon catheter from the first guide catheter;

(d) advancing Section 1 of the exchange device over the coronary guide wire into the coronary artery and proximal to the blockage;

(e) advancing Section 2 of the exchange device over the coronary guide wire to meet Section 1;

(f) connecting Section 1 and Section 2 of the exchange device with the connecting device;

(g) removing the first guide catheter over the exchange device without dislodging the coronary guide wire;

(h) advancing a second guide catheter over the exchange device into the coronary artery and proximal to the blockage; and (i) removing the exchange device.

The present invention also pertains to a guide catheter exchange device for exchanging a first guide catheter advanced over an over-the-wire balloon catheter and a coronary guide wire for a second guide catheter without removing the coronary guide wire in percutaneous transluminal coronary angioplasty wherein the exchange device comprises Section 1, Section 2, and a connecting device for connecting Section 1 and Section 2, wherein Section 1 is a hollow wire having a soft tip, an inner diameter from about 0.012 inches to about 0.020 inches, an outer diameter from about 0.030 inches to about 0.040 inches, and a length from about 120 centimeters to about 160 centimeters; and Section 2 is a hollow coiled wire having an inner diameter from about 0.012 inches to about 0.020 inches, an outer diameter from about 0.030 inches to about 0.040 inches, and a length from about 120 centimeters to about 160 centimeters.

In another embodiment, the present invention pertains to a method for exchanging a guide catheter employed by a monorail balloon catheter in percutaneous transluminal coronary angioplasty which comprises the steps of:

(a) providing a first guide catheter advanced over a monorail balloon catheter and a coronary guide wire, wherein the first guide catheter is in the ostium of a coronary artery and proximal to a blockage;

(b) providing a guide catheter exchange device comprising a wire having a length from about 200 centimeters to about 240 centimeters and an outer diameter from about 0.030 inches to about 0.040 inches, wherein a distal end of the exchange device is hollow, has a length from about 40 centimeters to about 60 centimeters, an inner diameter from about 0.012 inches to about 0.020 inches, and a side hole from about 40 centimeters to about 60 centimeters from the distal end of the exchange device through which the coronary guide wire may pass; and wherein a proximal end of the exchange device is hollow or solid, has an outer diameter from about 0.030 inches to about 0.040 inches, and a length from about 150 centimeters to about 200 centimeters;

(c) removing the monorail balloon catheter from the first guide catheter;

(d) advancing the exchange device over the coronary guide wire into the coronary artery and proximal to the blockage while passing the coronary guide wire out of the side hole of the exchange device;

(e) fastening the coronary guide wire to the exchange device by means of a securing device;

(f) removing the first guide catheter over the exchange device without dislodging the coronary guide wire;

(g) advancing a second guide catheter over the exchange device into the coronary artery and proximal to the blockage; and (h) unfastening the coronary guide wire from the exchange device and removing the exchange device.

The present invention also pertains to a guide catheter exchange device for exchanging a first guide catheter advanced over a monorail balloon catheter and a coronary guide wire for a second guide catheter without removing the coronary guide wire in percutaneous transluminal coronary angioplasty wherein the exchange device comprises a wire having a length from about 200 centimeters to about 240 centimeters and an outer diameter from about 0.030 inches to about 0.040 inches, wherein a distal end of the exchange device is hollow, has a length from about 40 centimeters to about 60 centimeters, an inner diameter from about 0.012 inches to about 0.020 inches, and a side hole from about 40 centimeters to about 60 centimeters from the distal end of the exchange device through which the coronary guide wire may pass; and wherein a proximal end of the exchange device is hollow or solid, has an outer diameter from about 0.030 inches to about 0.040 inches, and a length from about 150 centimeters to about 200 centimeters.

DETAILED DESCRIPTION OF THE INVENTION

In accord with the present invention, applicant has developed guide catheter exchange devices for exchanging a guide catheter while a coronary guide wire is across a blockage in a coronary artery without removing the coronary guide wire. In one embodiment, the guide catheter exchange device is employed for exchanging a first guide catheter advanced over an over-the-wire balloon catheter and a coronary guide wire for a second guide catheter. In this embodiment, the coronary guide wire is about 300 cm long, or has been extended to about 300 cm long. In another embodiment, the guide catheter exchange device is employed for exchanging a first guide catheter advanced over a monorail balloon catheter and a coronary guide wire for a second guide catheter.

The guide catheter exchange devices of the present invention can be better understood by reference to the Figures in which the same numerals refer to the same parts of the invention throughout the Figures. Although the present invention is described and illustrated in connection with preferred embodiments, applicant intends that modifications and variations may be used without departing from the spirit of the present invention.

FIG. 1 illustrates a conventional guide catheter advanced over an over-the-wire balloon catheter and a coronary guide wire. As set out in FIG. 1, a guide catheter (A) is positioned at the ostium of the coronary artery and does not enter it. The guide catheter (A) has an internal diameter from about 2 mm to about 3 mm and is about 100 centimeter long. Once this guide catheter (A) is positioned at the ostium of the coronary artery, an over-the-wire balloon catheter (B) is inserted through the guide catheter. Inside the over-the-wire balloon catheter (B) is a very fine wire called a coronary guide wire (C) which can vary in size from about 0.010 inch to about 0.018 inch in outer diameter and is usually from about 175 centimeters long to about 300 centimeters long.

Figure 2:
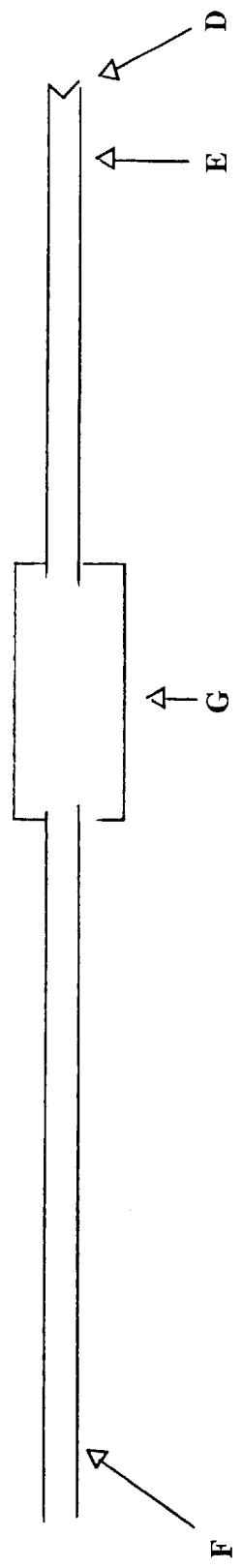
FIG. 2 illustrates a guide catheter exchange device of the present invention for use with an over-the-wire balloon catheter.

FIG. 2 illustrates a guide catheter exchange device of the present invention for use with an over-the-wire balloon catheter. In this embodiment, the coronary guide wire is about 300 cm long, or has been extended to about 300 cm long by conventional means. As set out in FIG. 2, the guide catheter exchange device comprises Section 1 (E), Section 2 (F), and a connecting device (G) for connecting Section 1 (E) and Section 2 (F). Section 1 (E) is the section which will enter the coronary arteries. Section 1 (E) is a hollow wire having an inner diameter from about 0.012 inches to about 0.020 inches, preferably about 0.020 inches, an outer diameter from about 0.030 inches to about 0.040 inches, preferably about 0.035 inches, and a length from about 120 centimeters to about 160 centimeters, preferably about 145 centimeters. Section 1 (E) of the exchange device will have a blunt tip (D), preferably a soft tip, about 20 mm long. Section 2 (F) is the section which will remain outside the body. Section 2 (F) is a hollow wire having an inner diameter from about 0.012 inches to about 0.020 inches, preferably about 0.020 inches, an outer diameter from about 0.030 inches to about 0.040 inches, preferably about 0.035 inches, and a length from about 120 centimeters to about 160 centimeters, preferably about 155 centimeters. Section 1 (E) and Section 2 (F) of the exchange device may be connected by any convenient connecting device (G), such as a locking nut over the wire, or a clasp. The exchange device is preferably stainless steel and is preferably coated on the outside with a material to make it smooth, such as Teflon. The diameter and length of the exchange device may be modified to suit a particular application.

The method for employing the guide catheter exchange devices of the present invention to exchange a guide catheter advanced over an over-the-wire balloon catheter and a coronary guide wire is as follows. First, the over-the-wire balloon catheter is removed from the first guide catheter which is in the ostium of a coronary artery and proximal to a blockage. Then, Section 1 of the exchange device is advanced over the coronary guide wire into the coronary artery and proximal to the blockage. Section 2 of the exchange device is then advanced over the coronary guide wire to meet Section 1. Section 1 and Section 2 of the exchange device are then connected with the connecting device. The first guide catheter is then removed over the exchange device without dislodging the coronary guide wire. The second guide catheter is then advanced over the exchange device into the coronary artery and proximal to the blockage. The exchange device may then be removed. An over-the-wire balloon catheter may then be advanced over the coronary guide wire and through the second guide catheter after the exchange device is removed. The guide catheter exchange device will provide adequate support to remove the initial guide catheter and to insert a new guide catheter without dislodging the coronary guide wire. In general, the guide catheter exchange devices of the present invention will be employed with coronary guide wires about 300 centimeters long which are across a blockage in a coronary artery.

Figure 3:
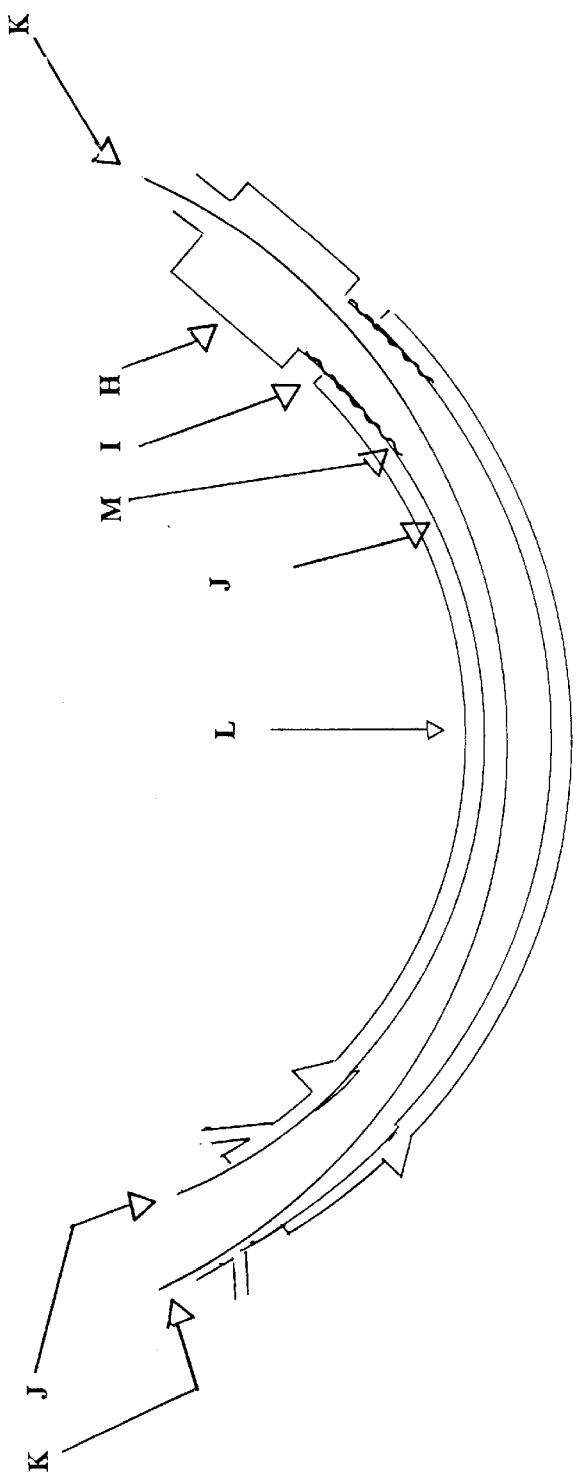
FIG. 3 illustrates a conventional guide catheter advanced over a monorail balloon catheter and a coronary guide wire.

In another embodiment, a guide catheter exchange device is employed for exchanging a guide catheter advanced over a monorail balloon catheter and a coronary guide wire. FIG. 3 illustrates a conventional guide catheter advanced over a monorail balloon catheter and a coronary guide wire. As set out in FIG. 3, a guide catheter (L) is positioned at the ostium of the coronary artery and does not enter it. Once this guide catheter (L) is positioned at the ostium of the coronary artery, a monorail balloon catheter (H) is inserted through the guide catheter. The balloon (H) in a monorail balloon catheter is connected by a soft tube (I) about 25 centimeters long to a hollow metallic tube (J). The total length of the monorail balloon catheter is about 145 centimeters. Inside the balloon catheter (H) is a very fine coronary guide wire (K) which can vary in size from about 0.010 inch to about 0.018 inch in outer diameter and is usually about 175 centimeters long. The coronary guide wire (K) enters the monorail balloon catheter at the distal tip and exits the monorail balloon catheter from a side hole (M) about 25 centimeters from the distal tip.

Figure 4:
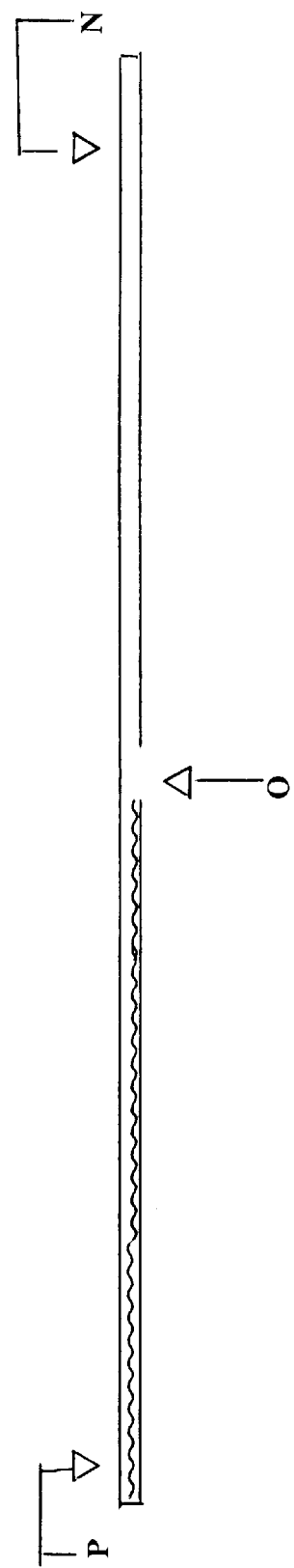
FIG. 4 illustrates a guide catheter exchange device of the present invention for use with a monorail balloon catheter.

FIG. 4 illustrates a guide catheter exchange device of the present invention for use with a monorail balloon catheter. As set out in FIG. 4, the guide catheter exchange device comprises a wire having a length from about 200 centimeters to about 240 centimeters, preferably about 220 centimeters, and an outer diameter from about 0.030 inches to about 0.040 inches, preferably about 0.035 inches. The distal end of the exchange device (N) is the section which will enter the coronary arteries. The distal end of the exchange device (N) is hollow, has a length from about 40 centimeters to about 60 centimeters, preferably about 50 centimeters, an inner diameter from about 0.012 inches to about 0.020 inches, preferably about 0.020 inches, and a side hole (O) from about 40 centimeters to about 60 centimeters, preferably about 50 centimeters, from the distal end of the exchange device through which the coronary guide wire may pass. The proximal end of the exchange device (P) is the section which will remain outside the body. The proximal end of the exchange device (P) is hollow or solid, has an outer diameter from about 0.030 inches to about 0.040 inches, preferably about 0.035 inches, and a length from about 150 centimeters to about 200 centimeters, preferably about 180 centimeters. The exchange device is preferably stainless steel and is preferably coated on the outside with a material to make it smooth, such as Teflon. The diameter and length of the exchange device may be modified to suit a particular application. The exchange device may further comprise a securing device on the proximal end of the exchange device to fasten the coronary guide wire to the exchange device. The fastening device in the exchange device may be a clasp or securing device.

The method for employing the guide catheter exchange devices of the present invention to exchange a guide catheter advanced over a monorail balloon catheter and a coronary guide wire is as follows. First, the monorail balloon catheter is removed from the first guide catheter which is in the ostium of a coronary artery and proximal to a blockage. Then, the exchange device is advanced over the coronary guide wire into the coronary artery and proximal to the blockage unit the coronary guide wire exits the side hole of the exchange device (FIG. 4, O). Once the coronary guide wire passes out of the side hole of the exchange device, the coronary guide wire can be held steady by simply grasping it and the exchange device advanced over the coronary guide wire into the proximal coronary artery. The coronary guide wire is then fastened to the exchange device by means of a securing device. The first guide catheter is then removed over the exchange device without dislodging the coronary guide wire. A second guide catheter is then advanced over the exchange device into the coronary artery and proximal to the blockage. The coronary guide wire is then unfastened from the exchange device and the exchange device is removed. A monorail balloon catheter may then be advanced over the coronary guide wire and through the second guide catheter after the exchange device is removed. The guide catheter exchange device will provide adequate support to remove the initial guide catheter and to insert a new guide catheter without dislodging the coronary guide wire. In general, the guide catheter exchange devices of the present invention will be employed with coronary guide wires about 175 centimeters long which are across a blockage in a coronary artery.

The invention being thus described, it will be obvious that the same may be varied in many ways. Such variations are not to be regarded as a departure from the spirit and scope of the invention and all such modifications are intended to be included within the scope of the following claims.

I claim:

1. A method for exchanging a guide catheter employed by an over-the-wire balloon catheter in percutaneous transluminal coronary angioplasty which comprises the steps of:
   (a) providing a first guide catheter advanced over an over-the-wire balloon catheter and a coronary guide wire, wherein the first guide catheter is in the ostium of a coronary artery and proximal to a blockage;
   (b) providing a guide catheter exchange device comprising Section 1, Section 2, and a connecting device for connecting Section 1 and Section 2; wherein Section 1 is a hollow wire having an inner diameter from about 0.012 inches to about 0.020 inches, an outer diameter from about 0.030 inches to about 0.040 inches, and a length from about 120 centimeters to about 160 centimeters; and Section 2 is a hollow wire having an inner diameter from about 0.012 inches to about 0.020 inches, an outer diameter from about 0.030 inches to about 0.040 inches, and a length from about 120 centimeters to about 160 centimeters;
   (c) removing the over-the-wire balloon catheter from the first guide catheter;
   (d) advancing Section 1 of the exchange device over the coronary guide wire into the coronary artery and proximal to the blockage;
   (e) advancing Section 2 of the exchange device over the coronary guide wire to meet Section 1;
   (f) connecting Section 1 and Section 2 of the exchange device with the connecting device;
   (g) removing the first guide catheter over the exchange device without dislodging the coronary guide wire;
   (h) advancing a second guide catheter over the exchange device into the coronary artery and proximal to the blockage; and
   (i) removing the exchange device.

2. The method according to claim 1, wherein Section 1 of the exchange device has an inner diameter of about 0.020 inches, an outer diameter of about 0.035 inches, and a length of about 145 centimeters.

3. The method according to claim 1, wherein Section 2 of the exchange device has an inner diameter of about 0.020 inches, an outer diameter of about 0.035 inches, and a length of about 155 centimeters.

4. The method according to claim 1, wherein the connecting device in the exchange device is a locking nut over the wire or a clasp.

5. The method according to claim 1, wherein the coronary guide wire is across a blockage in a coronary artery.

6. The method according to claim 1, wherein the coronary guide wire is about 300 centimeters long.

7. The method according to claim 1, further comprising the step of advancing an over-the-wire balloon catheter over the coronary guide wire and through the second guide catheter after the exchange device is removed.

8. A guide catheter exchange device for exchanging a first guide catheter advanced over an over-the-wire balloon catheter and a coronary guide wire for a second guide catheter without removing the coronary guide wire in percutaneous transluminal coronary angioplasty wherein the exchange device comprises Section 1, Section 2, and a connecting device for connecting Section 1 and Section 2, wherein Section 1 is a hollow wire having a soft tip, an inner diameter from about 0.012 inches to about 0.020 inches, an outer diameter from about 0.030 inches to about 0.040 inches, and a length from about 120 centimeters to about 160 centimeters; and Section 2 is a hollow coiled wire having an inner diameter from about 0.012 inches to about 0.020 inches, an outer diameter from about 0.030 inches to about 0.040 inches, and a length from about 120 centimeters to about 160 centimeters.

9. The exchange device according to claim 8, wherein Section 1 of the exchange device has an inner diameter of about 0.020 inches, an outer diameter of about 0.035 inches, and a length of about 145 centimeters.

10. The exchange device according to claim 8, wherein Section 2 of the exchange device has an inner diameter of about 0.020 inches, an outer diameter of about 0.035 inches, and a length of about 155 centimeters.

11. The exchange device according to claim 8, wherein the connecting device is a locking nut over the wire or a clasp.

* * * * *